United States Patent
Nakajima et al.

(10) Patent No.: US 7,112,292 B2
(45) Date of Patent: Sep. 26, 2006

(54) METHOD OF MANUFACTURING SEAMLESS CAPSULE

(75) Inventors: Hiroyuki Nakajima, Tokyo (JP);
Masayoshi Yamazaki, Tokyo (JP);
Takeshi Nakamura, Tokyo (JP);
Tsukasa Yamamoto, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 432 days.

(21) Appl. No.: 10/344,677

(22) PCT Filed: Aug. 16, 2001

(86) PCT No.: PCT/JP01/07054

§ 371 (c)(1),
(2), (4) Date: Feb. 14, 2003

(87) PCT Pub. No.: WO02/13755

PCT Pub. Date: Feb. 21, 2002

(65) Prior Publication Data

US 2003/0180485 A1    Sep. 25, 2003

(30) Foreign Application Priority Data

Aug. 17, 2000 (JP) .............................. 2000-247878

(51) Int. Cl.
*B29B 9/10* (2006.01)
(52) U.S. Cl. .............................................. 264/4; 264/9
(58) Field of Classification Search .................. 264/4, 264/9, 13, 14
See application file for complete search history.

(56) References Cited

U.S. PATENT DOCUMENTS

| | | | | |
|---|---|---|---|---|
| 5,223,185 A | * | 6/1993 | Takei et al. | 264/4 |
| 5,232,712 A | * | 8/1993 | Mills et al. | 425/133.1 |
| 5,650,232 A | * | 7/1997 | Glenn et al. | 428/402.2 |
| 5,888,538 A | * | 3/1999 | Kiefer et al. | 424/451 |
| 6,719,933 B1 | * | 4/2004 | Nakamura et al. | 264/14 |

FOREIGN PATENT DOCUMENTS

| | | |
|---|---|---|
| EP | 1 020 177 | 7/2000 |
| EP | 1 240 883 | 9/2002 |
| JP | 59-46540 | 3/1984 |
| JP | 362176536 | * 8/1987 |
| JP | 4-322741 | 11/1992 |
| JP | 4-338230 | 11/1992 |

(Continued)

*Primary Examiner*—Mary Lynn Theisen
(74) *Attorney, Agent, or Firm*—Morgan, Lewis & Bockius, LLP (57) ABSTRACT

Disclosed is a method of manufacturing a spherical seamless capsule formed by encapsulating a filler material such as a medicine with a capsule shell material such as gelatin. A concentric multiple nozzle is positioned above the liquid surface of a curing liquid such that the tip of the nozzle faces down. A concentric columnar composite flow which is discharged from this concentric multiple nozzle and which is composed of a filler material and a capsule shell material outside the filler material is immersed in the curing liquid, and cut in the curing liquid to form a droplet. The capsule shell material of the droplet is cured by the curing liquid, and thereby a seamless capsule is formed. Since, the droplet is not dropped into the curing liquid, no deformation of the droplet caused by collision against the liquid surface occurs. The tip of the multiple nozzle is positioned above the liquid surface of the curing liquid. This prevents water contained in the curing liquid from adhering to the surface of the nozzle and penetrating into the composite flow.

10 Claims, 5 Drawing Sheets

FOREIGN PATENT DOCUMENTS

| | | |
|---|---|---|
| JP | 5-317387 | 12/1993 |
| JP | 8-10313 | 1/1996 |
| JP | 11-188079 | 7/1999 |
| JP | 402229111 * | 9/1999 |
| JP | 2001-509 | 1/2001 |
| JP | 2001-9267 | 1/2001 |
| JP | 2001-238934 | 9/2001 |

\* cited by examiner

METHOD OF MANUFACTURING SEAMLESS CAPSULE

TECHNICAL FIELD

The present invention relates to a method of manufacturing a spherical seamless capsule formed by encapsulating a filler material such as a medicine, a flavor, a spice, or a fragrance with a capsule shell material such as gelatin.

BACKGROUND ART

Conventionally, a seamless capsule of the above-mentioned type is manufactured by a so-called air nozzle method, as disclosed in, e.g., Japanese Patent Laid-Open No. HEI4-338230, which uses a concentric multiple nozzle comprising a center nozzle and an annular nozzle which concentrically surrounds the center nozzle. That is, a liquid filler material is discharged from the center nozzle of the concentric multiple nozzle, and at the same time a liquid capsule shell material is discharged from the annular nozzle surrounding the center nozzle, thereby forming a composite flow having a concentric columnar form in which the capsule shell material flows so as to cover the outside of the filler material flow. A vibration is applied to the composite flow to cut the composite flow from its lower end in the air, thereby forming a droplet. This droplet is dropped onto the liquid surface of a curing liquid and brought into contact with the curing liquid to cure the capsule shell material. In this way, a spherical seamless capsule is manufactured by encapsulating the filler material with the capsule shell material.

The air nozzle method has the problem that the droplets cut in the air deform when they drop onto and collide against the liquid surface of the curing liquid, and this produces irregularity in the sphericity of manufactured seamless capsules.

It is, therefore, a main object of the present invention to provide a seamless capsule manufacturing method for obtaining high-quality seamless capsules without irregularity.

DISCLOSURE OF INVENTION

To achieve the above object, a method has been proposed in which the lower end portion of the concentric multiple nozzle is immersed in the curing liquid and the concentric columnar composite flow is discharged from the opening in the lower end of the nozzle into the curing liquid. In this submerged nozzle method, however, an S-shaped mark is formed on the surface of a seamless capsule. Therefore, the present inventors made extensive studies and have found that this S-shaped mark is occurred by water mixed and dispersed in the curing liquid. More specifically, water in the curing liquid adheres to and condenses on the outer surface of the lower end portion of the high-temperature concentric multiple nozzle immersed in the curing liquid. When this condensed water gradually grows to form a large droplet, this droplet falls along the outer surface and penetrates into the composite flow immediately after it is discharged from the tip or lower end of the nozzle, forming a longitudinal stripe in the direction of length on the circumferential surface of the composite flow. When a droplet formed by cutting the composite flow rotates in the curing liquid, an S-shaped mark is formed. The present inventors have found the above-mentioned fact.

The present invention made on the basis of this finding is a method of manufacturing a seamless capsule formed by encapsulating a filler material with a capsule shell material, characterized by comprising: a step of positioning a concentric multiple nozzle having a center nozzle and an annular nozzle concentrically surrounding the center nozzle, such that the tip of the concentric multiple nozzle is disposed above the liquid surface of a curing liquid and faces down; a step of supplying a liquid filler material to the center nozzle of the concentric multiple nozzle, and supplying a liquid capsule shell material to the annular nozzle of the concentric multiple nozzle; a step of immersing a concentric columnar composite flow, which includes the flow of the liquid filler material discharged from the center nozzle and the flow of the liquid capsule shell material discharged from the annular nozzle and flowing around said flow of the filler material, in the curing liquid; a step of cutting the composite flow immersed in the curing liquid from the end of the immersed composite flow, thereby forming a droplet; and a step of curing the capsule shell material of the droplet by coming into contact with the curing liquid.

Since in this method the droplet is not dropped into the curing liquid, no deformation of the droplet caused by collision against the liquid surface occurs. Also, the tip of the concentric multiple nozzle is positioned above the liquid surface of the curing liquid. This prevents water contained in the curing liquid from adhering to the nozzle surface and penetrating into the composite flow. Accordingly, S-shaped marks can also be prevented.

As the droplet forming means, a means which applies a vibration to the composite flow is preferred.

When the curing liquid is stored in a capsule forming tube, the position of immersion of the composite flow is preferably misaligned relative to the center of this capsule forming tube. In this case, a difference in curing liquid flow velocity is produced between the outside and inside of the capsule forming tube. This rotates the droplet and improves the shape of the droplet.

Furthermore, letting $\underline{d}$ be the outer diameter of the seamless capsule, it is effective to set the distance between the tip of the concentric multiple nozzle and the liquid surface of the curing liquid to 0.5 d to 3 d.

BEST MODES OF CARRYING OUT THE INVENTION

Figure 1:
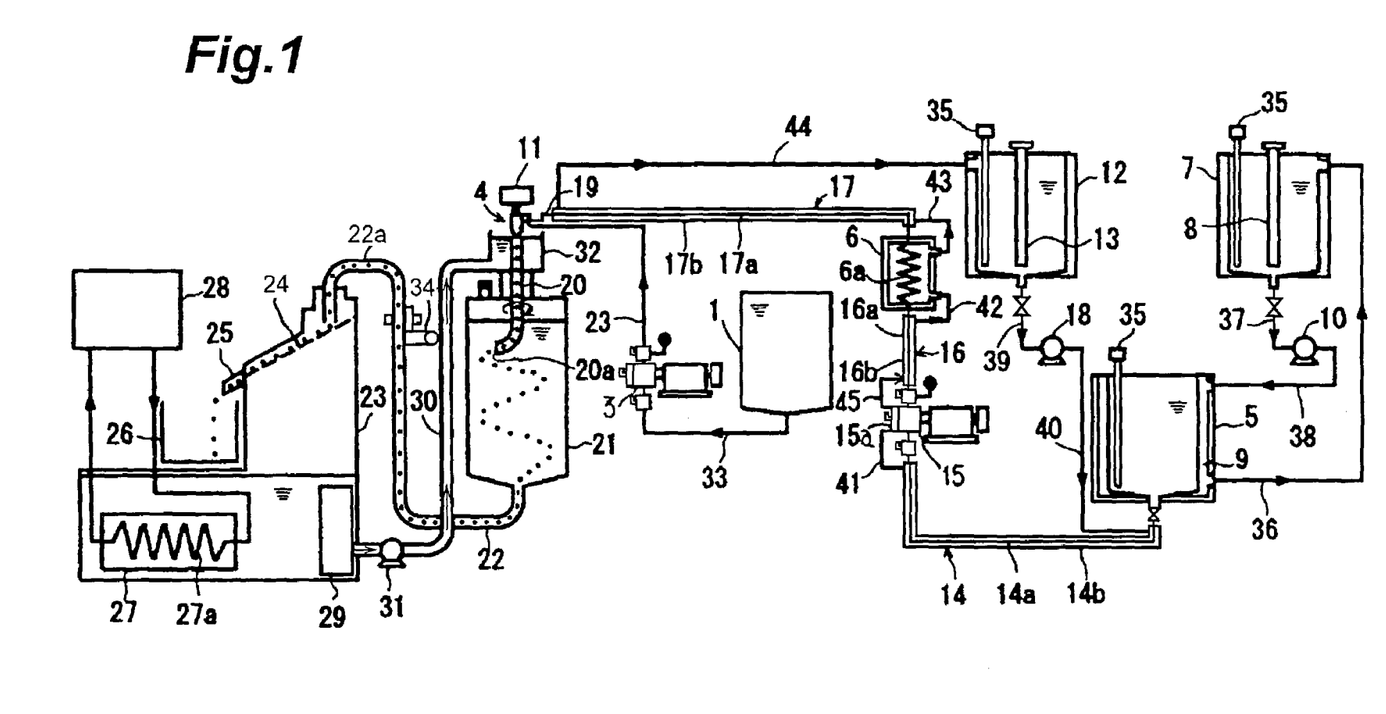
FIG. 1 is a schematic view showing a system for carrying out a seamless capsule manufacturing method according to the present invention.
Figure 2:
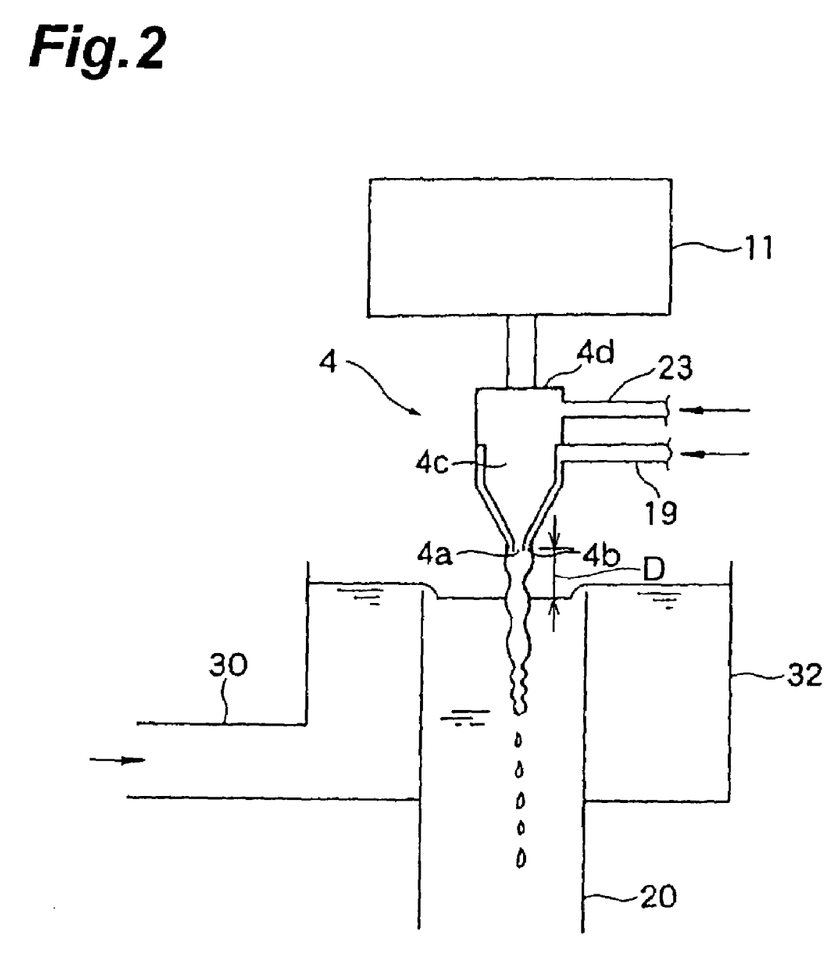
FIG. 2 is a partially enlarged view showing a concentric multiple nozzle used in the system shown in FIG. 1 and its vicinity.

Now, a preferred embodiment of the present invention will be described below with reference to the accompanying drawings. FIG. 1 schematically shows a system for carrying out a seamless capsule manufacturing method according to the present invention. FIG. 2 shows a concentric multiple nozzle used in this system and the peripheral construction of the nozzle in an enlarged scale.

In FIG. 1, reference numeral 1 indicates a filler tank which stores a liquid filler material (hereinafter referred to as a filler liquid) containing, e.g., a medicine, a flavor, a spice or a fragrance. This filler liquid within the filler tank 1 is extracted through tube 33 and supplied to a concentric multiple nozzle 4 through tube 23 by a variable discharge type filler pump 3. Since it is desirable for the flow of the filler liquid to the concentric multiple nozzle 4 to be as stable as possible, the filler pump 3 is preferably of a type which imparts no pulsation to the filler liquid flow.

In FIG. 1, reference numeral 5 indicates a gelatin tank (first tank) for storing a liquid capsule shell material (hereinafter referred to as a gelatin solution) containing a substance having a property of gelling from a sol state, e.g., gelatin, agar, carrageenan, or alginic acid, or a substance such as a gum like guar gum or xanthan gum.

While being stored in the gelatin tank 5, the gelatin solution is heated by hot water circulating within a hot-water jacket 9 provided around the tank 5, so as to be maintained at a predetermined temperature, e.g., 50° C.

The hot water which has decreased its temperature in the process of circulating within the hot-water jacket 9 is supplied to a first constant-temperature bath 7 through a tube 36. In the bath 7, a heater 8 heats the hot water to raise its temperature, and the heated hot water again circulates in the host-water jacket 9 through a tube 37, first hot-water pump 10, and tube 38.

The gelatin solution within the gelatin tank 5 is extracted trough an inner tube 14a of a double tube 14 by a variable discharge type gelatin pump 15 which forms no pulsation in the flow, and is supplied to the concentric multiple nozzle 4 after passing through an inner tube 16a of a double tube 16, a spiral tube 6a of an intermediate heater 6, an inner tube 17a of a double tube 17, and tube 19 in this order.

Hot water as a heating fluid is supplied into ane annular space between the inner tube 14a and an outer tube 14b of the double tube 14 from a flow inlet provided at the end portion of the tube 14 on the side of the gelatin tank 5. This hot water is maintained at a predetermined temperature by a heater 13 in a second constant-temperature tank 12 and supplied to the double tube 14 through tubes 39 and 40 by a second hot-water pump 18. The gelatin solution flowing in the inner tube 14a of the double tube 14 is heated by the hot water flowing between the inner tube 14a and outer tube 14b.

The hot water having flown into the annular space between the inner and outer tubes 14a and 14b flows into a hot-water jacket 15a of the gelatin pump 15 through a tube 41, and then flows into an annular space between the inner tube 16a and an outer tube 16b of the double tube 16 through a tube 45. In this process, the gelatin solution flowing through the inner tube 16a is heated by the hot water flowing between the inner and outer tubes 16a and 16b.

Subsequently, the hot water within the double tube 16 enters the intermediate heater 6 through a tube 42 and heats, while flowing about the spiral tube 6a, the gelatin solution flowing through the spiral tube 6a.

The hot water flowing out of the intermediate heater 6 enters an annular space between the inner tube 17a and an outer tube 17b of the double tube 17 through a tube 43 and heats, in the process of flowing through this space, the gelatin solution flowing through the inner tube 17a. Thereafter, the hot water flows out of the double tube 17, returns to the second constant-temperature bath 12 through a tube 44, and is again heated.

Hence, while flowing through the tubes 14a, 16a, 6a, and 17a from the gelatin tank 5 to the concentric multiple nozzle 4, the gelatin solution is heated by the hot water to gradually raise its temperature from 50° C. to a predetermined temperature, e.g., 80° C. This hot gelatin solution flows into the concentric multiple nozzle 4.

As shown in FIG. 2, the concentric multiple nozzle 4 has a center nozzle 4a which opens downward, and an annular nozzle 4b which concentrically surrounds the center nozzle 4a. The tips or lower ends of the center nozzle 4a and the annular nozzle 4b are positioned above the liquid surface of a curing liquid in a capsule forming tube 20. The curing liquid is a liquid for curing the gelatin solution by coming into contact therewith, and can be suitably selected from, e.g., medium-chain triglyceride, water, liquid paraffin, calcium solution, and vegetable oil such as soybean oil and olive oil.

In the upper portion of a chamber 4c in the concentric multiple nozzle 4 into which the filler liquid is introduced through the tube 23, a movable wall 4d is provided. The movable wall 4d is made of a flexible film or the like and defines a part of the wall portion of the chamber 4c. The movable wall 4d can be vertically moved by a vibrator 11 and can thereby apply vibrations having a predetermined period and amplitude to the filler liquid in the chamber 4c. This movement of the movable wall 4d generates a downward propagating ripple in the filler liquid.

The filler liquid supplied to the concentric multiple nozzle 4 flows out downward from the center nozzle 4a. At the same time, the gelatin solution supplied to the concentric multiple nozzle 4 flows out downward, in a form which surrounds the filler liquid, from the annular nozzle 4b.

Consequently, a concentric columnar composite flow comprising the filler liquid and the gelatin solution covering the circumferential surface of the filler liquid continuously flows out of the concentric multiple nozzle 4. The lower end of the composite flow is immersed in the curing liquid in the capsule forming tube 20. This immersion position is misaligned relative to the center of the capsule forming tube 20. More specifically, the capsule forming tube 20 is a tubular member having a vertical portion which extends vertically and has an open upper end. The vertical portion of the capsule forming tube 20 and the concentric multiple nozzle 4 are arranged such that their central axes are parallel to each other at a predetermined spacing between them. As will be described later, a reserve tank 32 is formed around the capsule forming tube 20, and the curing liquid is supplied to the reserve tank 32. Therefore, the curing liquid in the reserve tank 32 flows into the capsule forming tube 20 from the open upper end thereof, and flows down in the tube 20.

Then, vibrations of the movable wall 4d are transmitted to the composite flow via the filler liquid to sequentially cut the composite flow from its end in the curing liquid, thereby forming droplets in which the filler liquid is encupsulated with the gelatin solution.

Each droplet falls by gravity acting on it, together with the curing liquid flowing downward in the capsule forming tube 20. The flow velocity of the curing liquid flowing in the center of the capsule forming tube 20 is higher than the velocity of the curing liquid flow near the tube wall. Therefore, the droplet immersed and cut in the position misaligned relative to the center of the capsule forming tube 20 rotates by the flow velocity difference between the curing liquid flowing on the outside (tube wall side) of this droplet and the curing liquid flowing on the inside (the side of the center of the capsule forming tube 20) of this droplet.

While thus rotationally falling, the droplet gradually becomes spherical because of its surface tension and acquires a good outer appearance. Also, the gelatin solution on the surface of the droplet comes in contact with the curing liquid and cools and/or reacts with the curing liquid and gradually cures.

The effect of improving the outer appearance quality of the seamless capsule by rotation of the droplet inside the capsule forming tube 20 is obtained not only when the droplet is formed below the liquid surface of the curing liquid, but also when the droplet is formed above the liquid surface and then dropped into the curing liquid.

As shown in FIG. 1, the lower portion of the capsule forming tube 20 is horizontally curved. An opening 20a at the end (lower end) of the curved portion of the tube 20 is immersed in the curing liquid stored within a curing bath 21.

The capsule forming tube 20 is supported so as to be rotatable about its vertical axis, and is rotated by a motor (not shown). When the capsule forming tube 20 moderately rotates about its vertical axis, the curing liquid in the capsule forming tube 20 and its accompanying droplets horizontally flow out of the opening 20a. Consequently, in the curing liquid stored in the curing bath 21, the droplets are dispersed onto the circumference of a circle having a diameter slightly larger than that of the locus of rotation of the opening 20a. Then, while the droplets, moderately fall in the curing liquid, the gelatin solution sufficiently cures to form seamless capsules.

The seamless capsules which have fallen to the bottom of the curing bath 21 enter, together with the curing liquid, a transfer tube 22 connected to the opening in the bottom of the curing bath 21, and are fed to a separator 23 through the transfer tube 22. In the upper portion within the separator 23, a sieve plate 24 made of a porous plate, net or the like is obliquely disposed. The mesh of the sieve plate 24 is smaller than the outer diameter of the seamless capsule. Therefore, when the curing liquid and seamless capsules flow into the separator 23, the curing liquid passes through the sieve plate 24 and flows in the bottom of the separator 23 to be stored there. On the other hand, the seamless capsules roll on the sieve plate 24, drop into a collecting container 26 through a chute 25 to be stored there.

A cooler 27 is immersed in the curing liquid stored in the bottom portion of the separator 23. A coolant cooled by a refrigerator 28 circulates through a heat transfer tube 27a of the cooler 27. Accordingly, the curing liquid stored in the bottom of the separator 23 is cooled by exchanging heat with the coolant circulating in the heat transfer tube 27a of the cooler 27.

The curing liquid stored in the separator 23 is extracted from the bottom of the separator 23 through a filter 29 made of silica gel or the like, and enters the reserve tank 32 around the capsule forming tube 20 through a curing liquid tube 30 and a curing liquid pump 31 provided in the tube 30, and then flows over the upper edge of the reserve tank 32 into the capsule forming tube 20.

A portion of the transfer tube 22 attaining the highest position, i.e., an inverted U-shaped portion 22a is lower than the level of the curing liquid in the reserve tank 32. The difference between the inverted U-shaped portion 22a and the level of the curing liquid in the reserve tank 32 can be controlled by vertically moving the inverted U-shaped portion 22a by means of a vertical moving unit 34. In this way, it is possible to adjust the flow velocity of the curing liquid which flows through the transfer tube 22 from the capsule forming tube 20 by way of the curing bath 21.

Note that in FIG. 1, reference numeral 35 denotes a temperature sensor.

Figure 3:
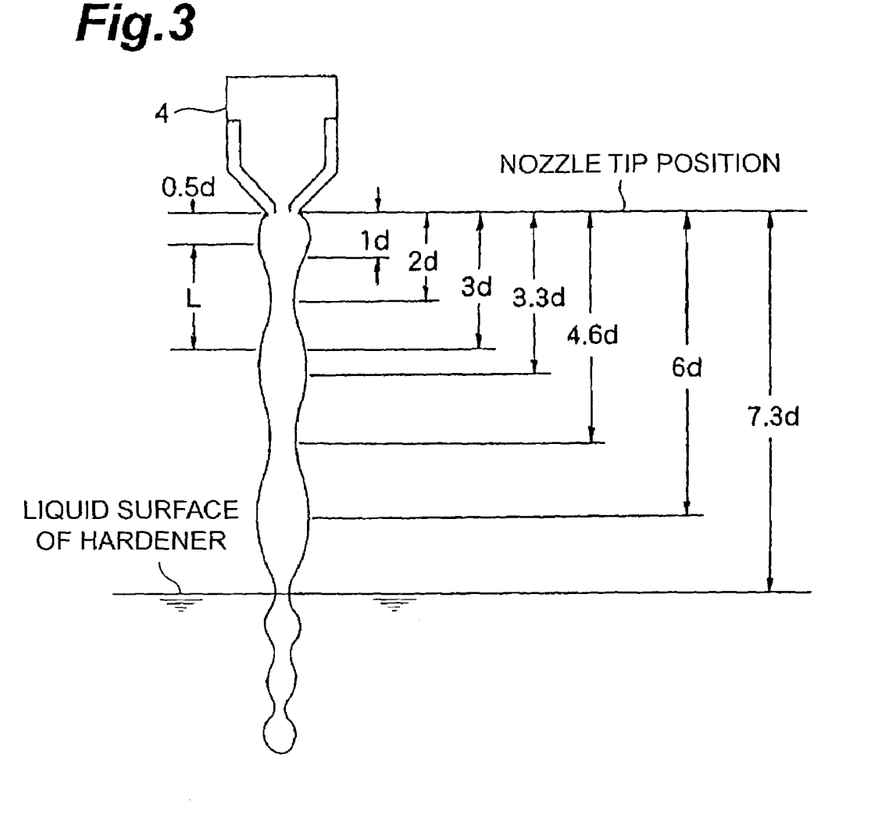
FIG. 3 is an enlarged schematic view of a composite flow.

FIG. 3 shows the results of observation of the concentric columnar composite flow which flows out of the concentric multiple nozzle 4 with vibrations applied. That is, FIG. 3 shows the state in which, letting $\underline{d}$ be the outside diameter of the seamless capsule, the upper end of the capsule forming tube 20 is positioned below the concentric multiple nozzle 4 with a distance 7.3 $\underline{d}$, and the composite flow flows down to this position of 7.3 $\underline{d}$ without contacting the curing liquid. Note that the outer diameter $\underline{d}$ of the seamless capsule is substantially determined by the flow velocity of the composite flow from the nozzle and the timing of vibration. Note also that the viscosity of the composite flow and the nozzle diameter have almost no influence on the outer diameter $\underline{d}$ of the seamless capsule.

The composite flow expands into a large diameter by the Barus effect at the tip of the concentric multiple nozzle 4, owing to the viscosity of this composite flow or the normal-stress effect. Hence, the composite flow gradually thins to a distance of about 2 d from the nozzle tip, gradually thickens from that position to a distance of about 3.3 d, gradually thins from that position to a distance of about 4.6 d, gradually thickens from that position to a distance of about 6 d, gradually thins from that position to a distance of about 7.3 d, and then is immersed in the curing liquid. Thereafter, the end portion of the composite flow is cut.

Figure 4:
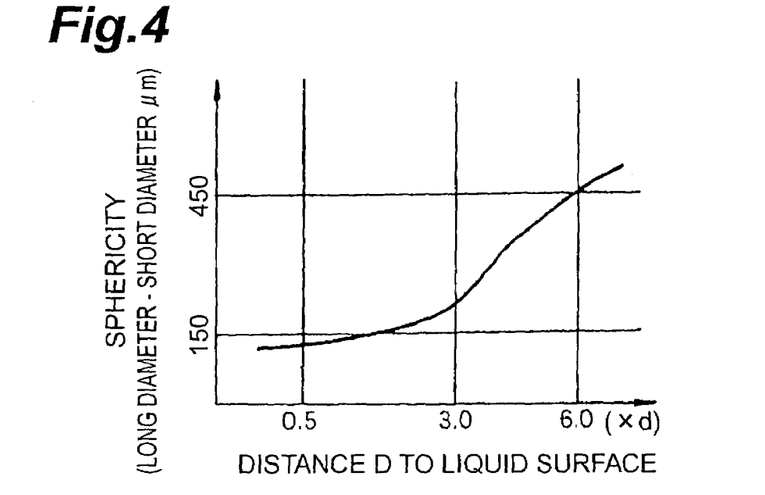
FIG. 4 is a graph showing the relationship between the nozzle tip-liquid surface distance and the sphericity.
Figure 5:
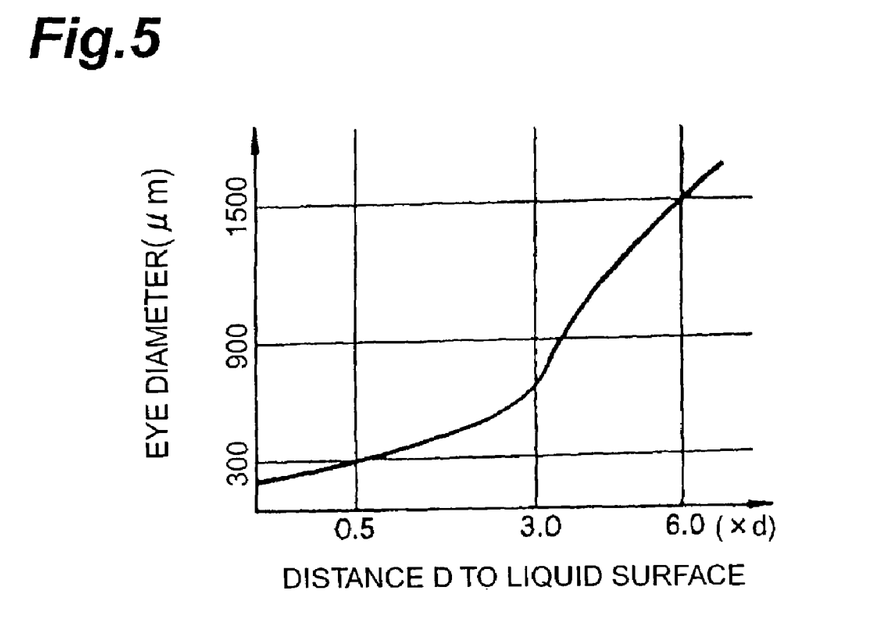
FIG. 5 is a graph showing the relationship between the nozzle tip-liquid surface distance and the eye-diameter.
Figure 6:
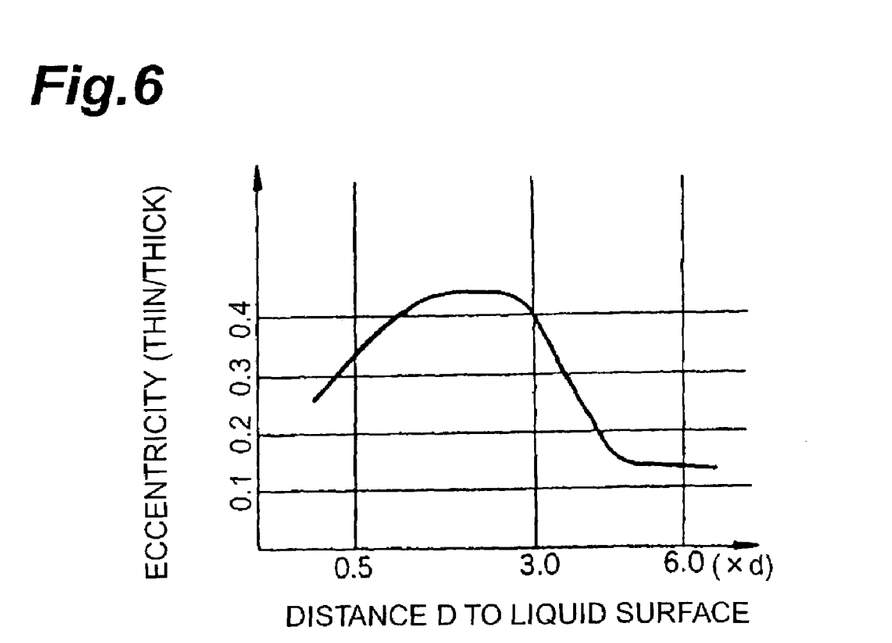
FIG. 6 is a graph showing the relationship between the nozzle tip-liquid surface distance and the eccentricity.

FIGS. 4, 5, and 6 show the results of measurements of the sphericity, eye-diameter, and eccentricity of the seamless capsule while a distance D (see FIG. 2) between the lower end of the concentric multiple nozzle 4 and the surface of the curing liquid in the capsule forming tube 20 is changed, respectively.

Figure 7:
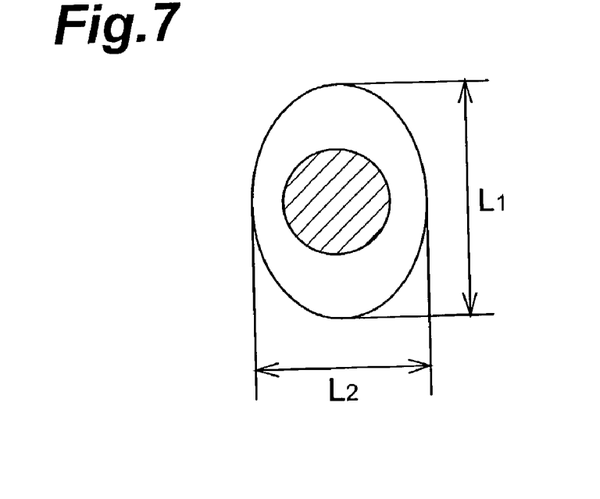
FIG. 7 is a view for explaining a seamless capsule having low sphericity.

When the difference between a long diameter $L_1$ and a short diameter $L_2$ of the seamless capsule is the smaller, the sphericity of the seamless capsule is the higher. When this difference is large as shown in FIG. 7, the sphericity is judged "low". As seen from FIG. 4, the difference between the long diameter $L_1$ and the short diameter $L_2$ of the seamless capsule abruptly increases, i.e., the sphericity worsens, when the distance D exceeds 3 d.

Figure 8:
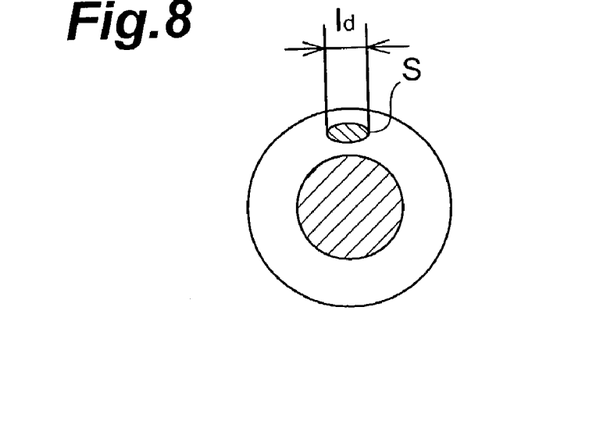
FIG. 8 is an explanatory view showing the eye in a seamless capsule.

Also, as seen from FIG. 5, the eye-diameter, i.e., a diameter Id of debris (so-called eye) S of the filler liquid formed in the film of the seamless capsule shown in FIG. 8 increases in the form of a steep curve from an inflection point at which the distance D is 3 d. Fortunately, the debris S called eyes is hardly formed.

Figure 9:
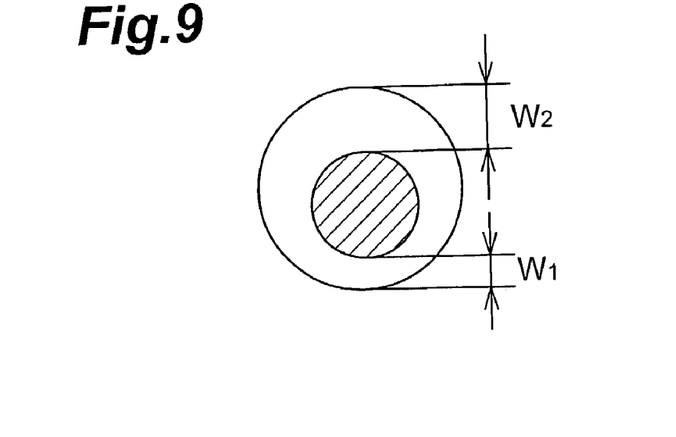
FIG. 9 is a view for explaining a seamless capsule having low eccentricity.

Furthermore, the eccentricity, i.e., the ratio ($W_1/W_2$) of a thickness $W_1$ of a thin portion to a thickness $W_2$ of a thick portion of the film of the seamless capsule, as shown in FIG. 9, gradually increases until the distance D becomes 2 d, is substantially constant when the distance D is 2 d to 3 d, and gradually decreases after the distance D becomes larger than 3 d.

It is seen from the above results that when the distance D is 0.5 d or less, the eccentricity of the seamless capsule is large, and this may result in a leak (liquid leak) of the liquid filler material, so this distance D is unsuitable. Also, when the distance D is 3 d or more, the sphericity is low, and this is undesirable in view of the product quality of the seamless capsule. In addition, when the distance D is 3 d or more, the eye diameter and eccentricity increased, thereby leading to a leak (liquid leak) of the liquid filler material, and air bubbles accompanied by the composite flow may be formed in the curing liquid.

On the other hand, it is seen that when the distance D is 0.5 d to 3 d, seamless capsules superior in all of the sphericity, eye-diameter, and eccentricity can be obtained. That is, it is possible to manufacture seamless capsules having an eye-diameter of 500 μm or less, an eccentricity of 0.5 or more, a sphericity of 150 μm or less, and a weight deviation RSD of 0.35% or less. Furthermore, it is possible to manufacture seamless capsules with which the appearance frequency of egg-shaped deformed capsules and capsules having S-shaped marks is 1 or 0 capsule per 2,400 capsules when visual inspection is performed.

Note that when the distance D is 2 d, i.e., in the first narrowed portion or small-diameter portion from above of the composite flow, this narrowed portion collides against the liquid surface to prevent the progress of the formation of spheres from this narrowed portion. As a consequence, the molding properties worsen to increase variations in the film weight. Therefore, the distance D is desirably 0.5 d to 1.5 d.

EXAMPLES

The results of tests 1, 2, and 3 conducted by operating the apparatus shown in FIGS. 1 and 2 under the conditions shown in Table 2 by using a filler liquid and gelatin solution having the formulas shown in Table 1 will be described below. Note that test 1 is an example of the present invention, and tests 2 and 3 are comparative examples.

TABLE 1

|  | per one capsule |
|---|---|
| <Filler Liquid> | |
| Alfacalcidol | 1 μg |
| Medium-chain triglyceride | 60 mg |
| (subtotal 60 mg) | |
| <Film> | |
| Gelatin | 30.8 mg |
| Glycerin | 9.2 mg |
| (subtotal 40.0 mg) | |
| Total | 100 mg |

TABLE 2

| Filling speed | Gelatin solution temperature at nozzle entrance | Temperature of curing liquid | Eccentric distance of nozzle | Vibration intensity |
|---|---|---|---|---|
| 35 capsules/sec | 86° C. | 7° C. | 3–5 mm | 4–7 dB |

In Table 2, the eccentric distance of the nozzle is the horizontal distance between the central axis of the concentric multiple nozzle and the central axis of the vertical portion of the capsule forming tube.

Under the conditions, in test 1, the distance between the tip of the concentric multiple nozzle and the liquid surface of the curing liquid was set to 1 d.

In test 2, the tip of the concentric multiple nozzle was immersed in the curing liquid.

In test 3, the distance between the tip of the concentric multiple nozzle and the liquid surface of the curing liquid was set to 5 d.

Tables 3 and 4 show the results of the physical property evaluation and visual inspection, respectively, of the seamless capsules obtained by tests 1, 2, and 3 as described above.

In the physical property evaluation, the eye-diameter, the eccentricity, the sphericity, and the weight deviation RSD of the total weight of the capsules immediately after filling (before drying) were calculated (n=10).

In the visual inspection, 2,400 capsules were extracted from the dried capsules and visually inspected to check the number of deformed capsules and the number of capsules having S-shaped marks.

TABLE 3

|  | Eye-diameter | Eccentricity[*1] | Sphericity[*2] | Weight deviation RSD |
|---|---|---|---|---|
| Test 1 (example) | 400 μm | 0.55 | 125 μm | 0.35% |
| Test 2 (comparative example) | 600 μm | 0.30 | 250 μm | 0.39% |
| Test 3 (comparative example) | 1400 μm | 0.13 | 350 μm | 0.50% |

[*1]Eccentricity = thickness ($W_1$)(μm) of thin portion of film/thickness ($W_2$) (μm) of thick portion of film
[*2]Sphericity = long diameter ($L_1$)(μm) of capsule − short diameter ($L_2$) (μm) of capsule

TABLE 4

|  | Number of egg-shaped deformed capsules | Number of capsules having S-shaped marks |
|---|---|---|
| Test 1 | 0/2400 | 0/2400 |
| Test 2 | 16/2400 | 2/2400 |
| Test 3 | 46/2400 | 0/2400 |

Good results were obtained for all the physical property values in test 1 in which the distance between the nozzle tip and the liquid surface of the curing liquid was set to 1d, compared to test 2 in which the nozzle tip was immersed in the curing liquid as the conventional method. In particular, the eye-diameter, eccentricity, and sphericity improved.

Also, egg-shaped deformed capsules and capsules having S-shaped marks found in test 2 were not found in test 1, i.e., excellent results were obtained in test 1.

On the other hand, in test 3 in which the distance between the nozzle tip and the liquid surface of the curing liquid was set to 5 d, all the physical property values were inferior to those in test 1, and egg-shaped deformed capsules were also found.

In the present invention as has been explained above, since the tip of the concentric multiple nozzle is positioned above the liquid surface of the curing liquid, unlike in the conventional submerged nozzle method, it is possible to reliably prevent a water droplet, which condenses and grows on the outer surface of the lower end portion of the concentric multiple nozzle, from penetrating into the composite flow and forming an S-shaped mark on the surface of a seamless capsule.

Also, since the tip of the concentric multiple nozzle faces downward and the lower end of the concentric columnar composite flow continuously discharged from the concentric multiple nozzle is immersed in the curing liquid and cut there, unlike in the conventional air nozzle method, it is possible to prevent deformation which may occur when a droplet cut in the air falls and collides against the liquid surface of the curing liquid, i.e., to prevent deterioration of the sphericity and eccentricity of a seamless capsule.

Additionally, in the case where, letting $\underline{d}$ be the outer diameter of a seamless capsule, the distance between the tip of the concentric multiple nozzle and the liquid surface of the curing liquid is set to 0.5 d to 3 d, it is possible to obtain a seamless capsule which well satisfies all the production standards such as the sphericity, eye-diameter, and eccentricity.

Furthermore, when the lower end of the concentric columnar composite flow is immersed into the curing liquid which flows down in the capsule forming tube such that the composite flow is misaligned relative to the center of the capsule forming tube, a droplet cut in the curing liquid can be well rotated in the curing liquid. This further improves the sphericity and eccentricity of a seamless capsule.

INDUSTRIAL APPLICABILITY

The present invention can efficiently manufacture seamless capsules having no defects. Accordingly, the present invention can be well utilized in the manufacturing industries of, e.g., medicines, sweets, and foods.

The invention claimed is:

1. A method of manufacturing a seamless capsule formed by encapsulating a filler material with a capsule shell material, said method comprising:
    a step of positioning a concentric multiple nozzle having a center nozzle and an annular nozzle concentrically surrounding the center nozzle, such that a tip of the concentric multiple nozzle is disposed above a liquid surface of a curing liquid with a space and faces down;
    a step of supplying a liquid filler material to the center nozzle of the concentric multiple nozzle, and supplying a liquid capsule shell material to the annular nozzle of the concentric multiple nozzle;
    a step of immersing a concentric columnar composite flow, which includes the flow of the liquid filler material discharged from the center nozzle and the flow of the liquid capsule shell material discharged from the annular nozzle and flowing around said flow of the filler material, in the curing liquid without separating into droplets before arriving at the liquid surface of the curing liquid;
    a step of cutting the composite flow immersed in the curing liquid from the end of the immersed composite flow, thereby forming a droplet; and
    a step of curing the capsule shell material of the droplet by coming into contact with the curing liquid.

2. A seamless capsule manufacturing method according to claim 1, wherein the droplet is formed by applying a vibration to the composite flow.

3. A seamless capsule manufacturing method according to claim 1 or 2, wherein the curing liquid is stored in a capsule forming tube, and the position of immersion of the composite flow is misaligned relative to the center of the capsule forming tube.

4. A seamless capsule manufacturing method according to claim 1, wherein letting d be the outer diameter of the seamless capsule, the distance between the tip of the concentric multiple nozzle and the liquid surface of the curing liquid is set between 0.5 d and 3 d.

5. A seamless capsule manufacturing method according to claim 4, wherein the droplet is formed by applying a vibration to the composite flow.

6. A seamless capsule manufacturing method according to claim 4 or 5, wherein the curing liquid is stored in a capsule forming tube, and the position of immersion of the composite flow is misaligned relative to the center of the capsule forming tube.

7. A method of manufacturing a seamless capsule formed by encapsulating a filler material with a capsule shell material, said method comprising:
    a step of preparing a concentric multiple nozzle having a center nozzle and an annular nozzle concentrically surrounding the center nozzle;
    a step of preparing a tubular member in which a curing liquid for curing a liquid capsule shell material by coming into contact with the capsule shell material flows, and said tubular member having a vertical portion which extends vertically and has an open upper end;
    a step of supplying a liquid filler material to the center nozzle of the concentric multiple nozzle, and supplying a liquid capsule shell material to the annular nozzle of the concentric multiple nozzle;
    a step of forming a concentric columnar composite flow which includes the flow of the liquid filler material discharged from the center nozzle and the flow of the liquid capsule shell material discharged from the annular nozzle and flowing around the flow of the filler material, and cutting the composite flow from the end thereof to form a droplet; and
    a step of introducing the droplet into the curing liquid in the vertical portion of the tubular member such that the position of introduction is horizontally misaligned relative to the center of the vertical portion, and curing the capsule shell material of the droplet by coming into contact with the curing liquid.

8. A seamless capsule manufacturing method according to claim 7, wherein the droplet is formed above the liquid surface of the curing liquid in the vertical portion of the tubular member.

9. A seamless capsule manufacturing method according to claim 7, wherein the droplet is formed below the liquid surface of the curing liquid in the vertical portion of the tubular member.

10. A seamless capsule manufacturing method according to any one of claims 7, 8 and 9, wherein the droplet is formed by applying a vibration to the composite flow.

* * * * *